(12) United States Patent
Wang et al.

(10) Patent No.: US 8,603,780 B2
(45) Date of Patent: Dec. 10, 2013

(54) METHODS AND COMPOSITIONS FOR ENHANCED EXPRESSION AND SECRETION OF PROTEINS

(75) Inventors: Zhuying Wang, Monmouth Junction, NJ (US); Xiaowu Liu, Nanjing (CN)

(73) Assignee: Nanjingjinsirui Science & Technology Biology Corp., Nanjing (CN)

( * ) Notice: Subject to any disclaimer, the term of this patent is extended or adjusted under 35 U.S.C. 154(b) by 0 days.

(21) Appl. No.: 13/550,120

(22) Filed: Jul. 16, 2012

(65) Prior Publication Data

US 2013/0017574 A1   Jan. 17, 2013

Related U.S. Application Data

(60) Provisional application No. 61/508,406, filed on Jul. 15, 2011.

(51) Int. Cl.
*A61K 38/00* (2006.01)

(52) U.S. Cl.
USPC ........ 435/70.1; 435/69.1; 435/69.8; 435/69.7

(58) Field of Classification Search
None
See application file for complete search history.

(56) References Cited

PUBLICATIONS

Cebe et al. "Rapid and easy thermodynamic optimization of the 5'-end of mRNA dramatically increases the level of wild type protein expression in *Escherichia coli*" Protein Expression and Purification 45 (2006) 374-380.*

* cited by examiner

*Primary Examiner* — John S Brusca
*Assistant Examiner* — Gerard Lacourciere
(74) *Attorney, Agent, or Firm* — Panitch Schwarze Belisario & Nadel LLP

(57) ABSTRACT

Optimized signal peptide coding sequences for enhanced expression and secretion of protein from a cell and related compositions and methods are described. The optimized signal peptide coding sequence encodes an mRNA that contains at least one hairpin structure immediately downstream of the initiation codon. Methods for obtaining the optimized signal peptide coding sequences and methods for enhanced expression and secretion of proteins using the optimized signal peptide coding sequences are also described.

20 Claims, 2 Drawing Sheets

METHODS AND COMPOSITIONS FOR ENHANCED EXPRESSION AND SECRETION OF PROTEINS

CROSS-REFERENCE TO RELATED APPLICATIONS

This application claims the benefit under 35 U.S.C. §119 (e) of U.S. Provisional Application No. 61/508,406, filed Jul. 15, 2011, the entire disclosure of all of these applications is hereby incorporated herein by reference.

FIELD OF THE INVENTION

The invention relates to protein expression and secretion from cells. In particular, embodiments of the present invention relate to optimized coding sequences for signal peptide and their use for enhanced protein expression and secretion from cells as well as other related compositions and methods.

BACKGROUND OF THE INVENTION

Recombinant protein expression has become a major tool in molecular biology. Recombinant expression of genes from transformed organisms is now a non-dispensable method for production of proteins for various purposes, such as protein characterization, protein identification, protein function and structure study, etc. Recombinant expression of genes has also been utilized for large scale production of proteins for commercial purposes, such as, to be used as enzymes, nutritional proteins, biopharmaceuticals (drugs), etc.

A recombinant DNA encoding a protein (polypeptide) can be introduced into a "host" cell where it is expressed and translated into the protein, which is stored inside the cell, e.g., in the cytoplasm or cytosol of the cell, and subsequently isolated or purified from the host cell. However, this procedure has some disadvantages. For example, the recombinant polypeptide may be toxic to the host cell and may even kill the host cell as the polypeptide is continuously synthesized in the cell and begins to accumulate. The recombinant polypeptide may also be degraded by intracellular proteases or be subject to unwanted post-translational modification, such as acetylation, etc. In addition, as the intracellular concentration of the recombinant polypeptide increases, the host cell machinery may slow down or cease manufacturing via a "feedback mechanism" directing termination of polypeptide synthesis, see, e.g., U.S. Pat. No. 5,470,719.

Exporting or secreting a recombinant protein outside the cell can overcome the problems associated with the accumulation of the protein in the cell. Furthermore, because the protein can be harvested fairly easily from the chemically much simpler extracellular environment, it is preferred for the recombinant protein to be secreted into the extracellular environment for easy downstream processing.

There remains a need for enhanced expression and secretion of proteins from the cells.

BRIEF SUMMARY OF THE INVENTION

It is now discovered that protein expression and secretion are regulated not only by the amino acid sequence of the signal peptide, but also by a secondary structure of messenger RNA (mRNA) that translates into the signal peptide. According to embodiments of the present invention, the presence of at least one hairpin structure in a region of the mRNA immediately downstream of the start codon significantly enhances protein expression and secretion.

Thus, in one general aspect, the present invention relates to an isolated nucleic acid molecule for enhanced recombinant expression and secretion of a polypeptide from a cell. The nucleic acid molecule comprises a first polynucleotide sequence encoding a signal peptide operably linked to a second polynucleotide sequence encoding the polypeptide, wherein the first polynucleotide sequence and the second polynucleotide sequence are not endogenously operably linked in the cell, the first polynucleotide encodes a messenger RNA (mRNA) that comprises at least one hairpin structure immediately downstream of the initiation codon, and when expressed in the cell, the signal peptide directs the secretion of the polypeptide from the cell, resulting in enhanced recombinant expression and secretion of the polypeptide from the cell.

In another general aspect, the present invention relates to an isolated nucleic acid molecule comprising a polynucleotide having at least about 55%, 60%, 65%, 70%, 75%, 80%, 85%, 90%, 95% or 100% sequence identity to SEQ ID NO: 1, wherein the polynucleotide encodes an mRNA having at least one hairpin structure immediately downstream of the initiation codon, and the polynucleotide encodes a signal peptide.

Another aspect of the present invention relates to a method of obtaining an optimized polynucleotide encoding an optimized signal peptide for enhanced recombinant expression and secretion of a polypeptide, the method comprising:
  obtaining a polynucleotide encoding a signal peptide; and
  substituting one or more nucleotides in the polynucleotide to obtain the optimized polynucleotide encoding the optimized signal peptide, and the optimized polynucleotide encoding a messenger RNA comprising at least one hairpin structure immediately downstream of the initiation codon.

Other general aspects of the present invention relate to vectors and recombinant cells comprising an isolated nucleic acid molecule according to an embodiment of the present invention, and related methods for enhanced recombinant expression and secretion of a polypeptide from a cell.

According to preferred embodiments of the present invention, the optimized polynucleotide comprises SEQ ID NO:1, which directs enhanced recombinant expression and secretion of a polypeptide from a cell.

The details of one or more embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

DETAILED DESCRIPTION OF THE INVENTION

Figure 1:
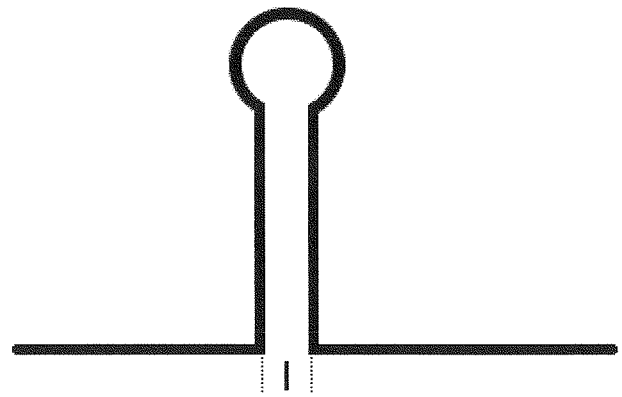
FIG. 1 is a graph depicting an mRNA for a secreted protein according to an embodiment of the present application, the mRNA has a single hairpin structure (I) immediately downstream of the AUG start codon within the coding region for the signal peptide.
Figure 2:
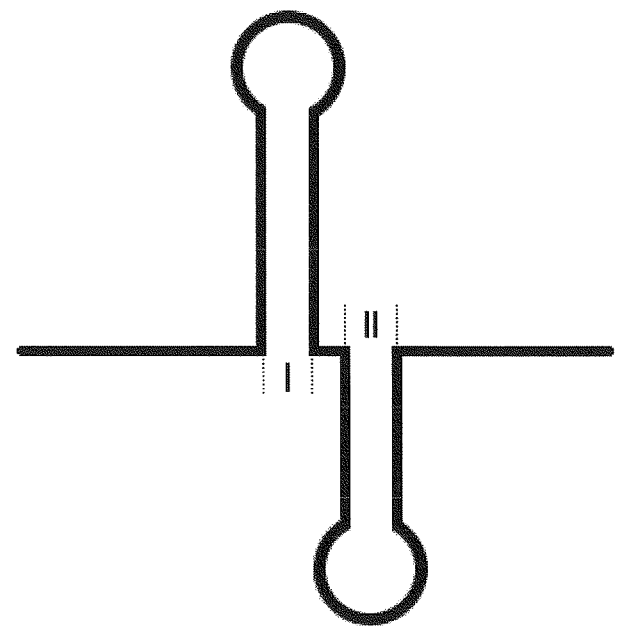
FIG. 2 is a graph depicting an mRNA for a secreted protein according to another embodiment of the present application, the mRNA has two adjacent hairpin structures (I) and (II) immediately downstream of the AUG start codon within the coding region for the signal peptide, the two hairpin structures can be located about 1 to 10 nucleotides apart.
Figure 3:
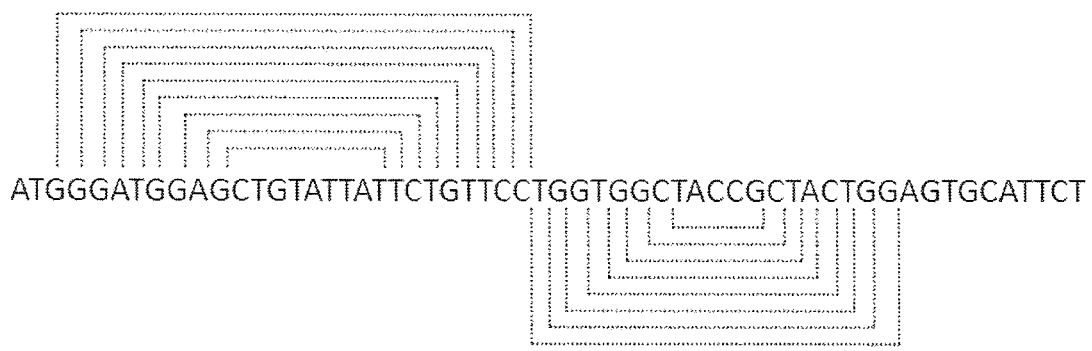
FIG. 3 depicts the nucleotide sequence of an inventive signal peptide coding sequence (SEQ ID NO: 1) according to an embodiment of the present invention that is useful in enhancing the expression and secretion of polypeptides: C at position 28 can participate in the formation of either the first hairpin or second hairpin structure; and the dotted line stands for possible base pairing in the two hairpin structures.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, a "hairpin", a "hairpin loop", a "bulge", "5'-UTR", a "secondary structure", "operably linked", "signal peptide", "polynucleotide", "polypeptide", or "protein" are to be taken in their broadest context. A hairpin structure can vary by containing not only a stem and a loop but also one or more bulges. The terms "hairpin" and "hairpin loop" are used interchangeably. The terms "polypeptide" and "protein", which include antibodies, are used interchangeably.

A secreted polypeptide is typically made from a precursor protein containing a special N-terminal sequence, a signal peptide, also known as a leader peptide, leader sequence, signal sequence, targeting signal, transit peptide, or localization signal. The signal peptide is typically a short (about 3-60 amino acids, more typically 15-40 amino acids, long) peptide chain that directs the transportation or secretion of the protein. After directing the secreted polypeptide across the cell membrane, the signal peptide is normally removed from the secreted polypeptide by a signal peptidase.

In general, the signal peptide includes the initiation methionine and three distinct physicochemical regions: a positively charged N-terminus region, a central hydrophobic region (H-region), and a C-terminus region ending with a signal cleavage site (Steve Barash, Wei Wang, and Yanggu Shi (May 2002), "Human secretory signal peptide description by hidden Markov model and generation of a strong artificial signal peptide for secreted protein expression", *Biochemical and Biophysical Research Communications* 294 (2002): 835-842). Individual signal peptides show a low degree of sequence conservation (Von Heijine, 1988, *Biochim. Biophys. Acta* 947: 307-333)

Optimization of amino acid sequences of signal peptide has been the focus for increasing secretion and expression of a target secreted polypeptide. For example, Ravn studied 18 variants of the signal peptide SP310 from the bacterium *Lactococcus lactis* to learn more about the effect on protein secretion of amino acid alterations in the three regions of signal peptide (Peter Ravn, et al., 2003, "Optimization of signal peptide SP310 for heterologous protein production in *Lactococcus Lactis, Microbiology* 149:2193-2201). Studies on 16 signal peptides of difference amino acid sequences demonstrated that the actual choice of a signal peptide could have a considerable impact on the amount of protein expressed/secreted from mammalian cells (Stern, et al., 2007, "Improving mammalian cell factories: The selection of signal peptide has a major impact on recombinant protein synthesis and secretion in mammalian cells", *Trends Cell Mol. Biol.* 2: 1-17).

It was surprisingly discovered during the present invention that a secondary structure of the mRNA at the signal peptide coding region can enhance expression and secretion of a polypeptide operably linked to the signal peptide. The inventive secondary structures of mRNAs at the signal peptide coding region include, but are not limited to, at least one hairpin structure immediately downstream of the start codon, AUG. The region immediately downstream of the AUG start codon is translated into the N-terminal end of the signal peptide, thus is different from the 5'-UTR of the mRNA, which is not translated. Also, unlike the hairpin secondary structure at the 5'-UTR of mRNA, which may affect transcription or translation, the hairpin secondary structures at the signal peptide coding region of mRNA can enhance protein expression and secretion.

In one general aspect, the present invention relates to an isolated nucleic acid molecule for enhanced recombinant expression and secretion of a polypeptide from a cell. The nucleic acid molecule comprises a first polynucleotide sequence encoding a signal peptide operably linked to a second polynucleotide sequence encoding the polypeptide, wherein the first polynucleotide sequence and the second polynucleotide sequence are not endogenously operably linked in the cell, the first polynucleotide encodes a messenger RNA (mRNA) that comprises at least one hairpin structure immediately downstream of the initiation codon, and when expressed in the cell, the signal peptide directs the secretion of the polypeptide from the cell, resulting in enhanced recombinant expression and secretion of the polypeptide from the cell.

As used herein, "enhanced recombinant expression and secretion" means that when expressed in a cell under identical assay conditions, an isolated nucleic acid molecule according to an embodiment of the present invention results in more secreted polypeptide from the cell than an otherwise identical nucleic acid molecule that encodes the identical signal peptide and the identical secreted polypeptide, but not the identical mRNA. The mRNA encoded by the otherwise identical nucleic acid molecule does not contain the at least one hairpin structure immediately downstream of the initiation codon.

In view of the present disclosure, various prediction models and algorithms can be used to predict or design the signal sequences. See, e.g., Chou K C, *Curr Protein Pept Sci.* 2002 December; 3(6):615-22.

A hairpin or hairpin loop is formed by base pairing between adjacent (inverted) complementary sequences in a single strand nucleic acid, i.e., DNA or RNA. The hairpin consists of a base-paired, double-helical region, i.e., the stem, with a loop of unpaired bases at one end. The stem can be formed as a perfect duplex structure, i.e., between completely complementary sequences. The stem can also be formed between not perfectly complementary sequences. The length of the stem varies. Preferably, the hairpin structure in a nucleic acid molecule of the present invention comprises a stem of about 6 to 25 base pairs, such as 6, 7, 8, 9, 10, 12, 15, 20, 25, etc. base pairs.

The stability of the hairpin can be measured by the amount of free energy released to form the base paired structure. The free energy of the hairpin can be calculated using methods known in the art in view of the present disclosure. For example, the stability of the hairpin structure can be measured using the mfold program (Mathews et al (1999), "Expanded Sequence Dependence of Thermodynamic Parameters Improves Prediction of RNA Secondary Structure" *J. Mol. Biol.* 288:911-940). As known to those skilled in the art, the free energy or stability of a hairpin is influenced by the nucleotide sequence, such as individual base pairs within the hairpin and the relationship between the adjacent base pairs. The stability of a potential double helix is determined by the free energy calculation, which must produce a significantly negative value overall, or the secondary structure will unable to form.

In a preferred embodiment according to the present invention, the hairpin has a free energy ($\Delta G$) of about $-30$ Kcal/mol to about $-6.8$ Kcal/mol. Examples of hairpins suitable for the present invention include, but are not limited to, those having a free energy ($\Delta G$) of about $-30$, $-25$, $-20$, $-15$, $-10$ or $-6.8$ Kcal/mol.

According to an embodiment of the present invention, the first polynucleotide sequence encodes a messenger RNA that comprises one hairpin structure immediately downstream of the initiation codon. The hairpin has a free energy ($\Delta G$) of about $-30$ Kcal/mol to about $-6.8$ Kcal/mol.

According to another embodiment of the present invention, the first polynucleotide sequence encodes a messenger RNA that comprises two or more adjacent hairpin structures immediately downstream of the start codon. Each hairpin has a free energy ($\Delta G$) of about $-30$ Kcal/mol to about $-6.8$ Kcal/mol. In the first polynucleotide sequence, one or more nucleotides, such as about 1 to 10 nucleotides, can participate in the formation of either of the two adjacent hairpin structures. The two adjacent hairpins can be located a few nucleotides apart, such as 1, 2, 3, 4, 5, 6, 7, 8, 9, 10, etc., nucleotides apart.

Another aspect of the present invention relates to a method of obtaining an optimized polynucleotide that encodes an optimized signal peptide for enhanced recombinant expression and secretion of a polypeptide, the method comprising:
obtaining a polynucleotide encoding a signal peptide; and
substituting one or more nucleotides in the polynucleotide to obtain the optimized polynucleotide encoding the optimized signal peptide, and the optimized polynucleotide encoding a messenger RNA comprising at least one hairpin structure immediately downstream of the initiation codon.

In one embodiment of the present invention, the substituting step comprises synonymous substitution. Codon usage of the signal peptide can be altered by using different, but synonymous codons, so as to form secondary structures in the mRNA, such as hairpins just downstream of AUG (start codon), to increase the yield of recombinant expression and secretion of proteins from cells without altering the signal peptide amino acid sequence. The optimized polynucleotide encodes a signal peptide identical to the original signal peptide sequence, such as an endogenous or wild type signal peptide sequence.

In another embodiment of the present invention, the signal peptide coding sequence can be optimized for increased protein expression and secretion at both the mRNA and the protein levels. The optimized signal peptide coding sequence encodes an mRNA containing the secondary structure optimized for protein expression, such as the at least one hairpin structure immediately downstream of the start codon. The optimized signal peptide coding sequence also encodes a signal peptide containing the amino acid sequence optimized for protein expression and secretion, such as the amino acids optimized for protein expression and secretion known to those in the art. See, e.g., Peter Ravn, et al., 2003 and Stern, et al., 2007 above, which are incorporated herein by reference.

In view of the present disclosure, for any given signal peptides, the corresponding mRNA secondary structures can be predicted, for example, using a program such as mfold program. As known to those skilled in the art, an amino acid can be encoded by more than one codon (synonymous codons). Therefore, the preferred mRNA hairpin structures at signal peptide coding regions can be formed by using synonymous codons without affecting amino acid sequences of signal peptides. There may be cases where the preferred mRNA hairpin structures at signal peptide regions cannot be formed even using synonymous codons. In these cases, one or more of the amino acids of signal peptides can be mutated to other amino acids, preferably those amino acids optimized for protein secretion at protein level, and then the preferred mRNA hairpin structures at signal peptide coding regions can be formed. The amino acid sequences of signal peptide central hydrophobic region (H-region) are highly variable (Q. A. Valent, D. A. Kendall, S. High, R. Kusters, B. Oudega, J. Luirink (1995), *EMBO J.* 14:5494-5505). Thus, one or more amino acids in the H-region can be substituted, e.g., to amino acids optimized for protein expression and secretion or to other amino acids, in order to obtain at least one hairpin structure immediately downstream of the start codon in the mRNA.

According to an embodiment of the present invention, an optimized signal peptide coding sequence (SEQ ID NO. 1) is obtained based on the native or original signal peptide coding sequence (SEQ ID NO. 3) (see GenBank: ACCESSION: J00536) for mouse Ig H-chain V-region 3 signal peptide. SEQ ID NO:1 and SEQ ID NO:3 encode the same amino acid sequence SEQ ID NO:2 (MGWSCIELFLVATATGVHS), which is identical to the native or original signal peptide for the mouse Ig H-chain V-region 3 signal peptide (see UniProtKB database: ACCESSION: P01749).

It is well known in the art that some alterations in a polypeptide or polynucleotide sequence do not affect the functional properties of the polypeptide or polynucleotide. These alterations include, but are not limited to, substitutions, deletions and additions, etc. Therefore, the invention encompasses more than the specific exemplary sequences.

In another general aspect, the present invention relates to an isolated nucleic acid molecule comprising a polynucleotide having at least about 55%, 60%, 65%, 70%, 75%, 80%, 85%, 90%, 95% or 100% sequence identity to SEQ ID NO: 1, wherein the polynucleotide encodes an mRNA having at least one hairpin structure immediately downstream of the initiation codon, and the polynucleotide encodes a signal peptide.

Another general aspect of the present invention relates to a method of obtaining enhanced recombinant expression and secretion of a polypeptide from a cell. The method comprises:

obtaining a nucleic acid molecule according to an embodiment of the present invention; introducing the nucleic acid molecule into the cell to obtain a recombinant cell; and growing the recombinant cell under conditions to allow enhanced recombinant expression and secretion of the polypeptide from a cell.

In one embodiment of the present invention, the method further comprises isolating the polypeptide from the extracellular environment of the cell, such as the supernatant of the cell.

A nucleic acid molecule according to an embodiment of the present invention contains a first polynucleotide operably linked to a second polynucleotide. The first polynucleotide encodes a signal peptide and a messenger RNA comprising at least one hairpin structure immediately downstream of the initiation codon in the signal peptide coding region. The second polynucleotide encodes the polypeptide of interested.

In view of the present disclosure, the nucleic acid molecule can be obtained using any molecular biology method know in the art. Those skilled in the art will know how to operably link the inventive optimized signal peptide coding sequence, such as SEQ ID No: 1, to a coding sequence for a polypeptide of interest to thereby obtain a nucleic acid molecule according to an embodiment of the present invention.

The nucleic acid molecule can be made as part of an expression vector. The vector can be introduced into a suitable host cell to obtain a recombinant cell. The recombinant cell can be grown under conditions suitable for the expression and secretion of the polypeptide of interest.

Any polypeptide of interest can be expressed and secreted by the present method. Examples of such polypeptides include, but are not limited to, Herceptin (trastuzumab), Erbitux, Avastin (bevacizumab), Humira (adalimumab), Rituxan (rituximab), Lantus (insulin glargine), Factor IX, Factor VIII, γ-Interferon, Interleukin 2, Human growth hormone (HGH), Tissue plamsinogen activator (TPA), Epo (Erythropoietin), Aranesp, etc.

The host cell can be any suitable cell, such as a bacterial cell, a yeast cell, a plant cell or a mammalian cell. In a preferred embodiment, the host cell is a mammalian cell, more preferably, a human cell.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples of the methods of the invention are further illustrative of the nature of the invention, it needs to be understood that the invention is not limited thereto.

Example I

A recombinant DNA molecule encoding the heavy and light chains of Herceptin antibody with a C-terminal His tag was constructed using an optimized signal peptide coding sequence (SEQ ID NO:1) that encodes an N-terminal signal peptide (SEQ ID NO: 2). The recombinant DNA molecule was cloned into a mammalian expression vector for transient transfection into HEK293 serum free cells. Another recombinant DNA molecule encoding the heavy and light chains of Herceptin antibody with the C-terminal His tag was constructed using a wild-type signal peptide coding sequence (SEQ ID NO:3) that encodes the same N-terminal signal peptide (SEQ ID NO: 2). The recombinant DNA molecule was cloned into the same mammalian expression vector for transient transfection into the HEK293 serum free cells as a control.

The supernatants of transfected HEK293 cell cultures were analyzed by ELISA and Western blot. The primary antibody for Western blot was Mouse-anti-His mAb (GenScript, Cat. No. A00186). The reference standard for ELISA was Human IgG1 kappa (Sigma, Cat No. I5154).

Figure 4:
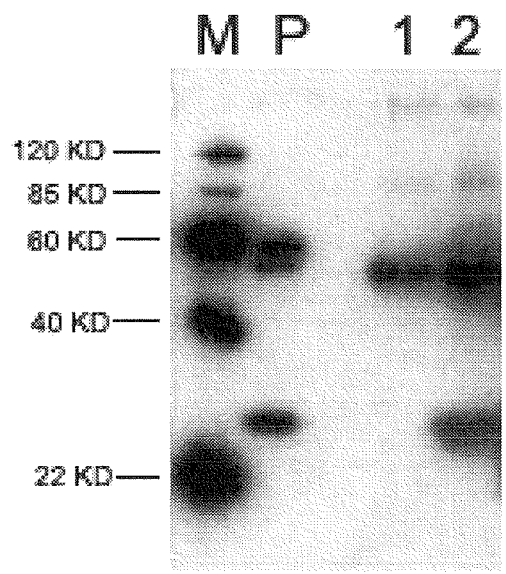
FIG. 4 demonstrates that an improved signal peptide coding sequence according to an embodiment of the present invention enhanced the expression and secretion of Herceptin antibody as analyzed by SDS-PAGE electrophoresis followed by Western blot: Lane M, a protein standard; Lane P, the reference standard for ELISA, human IgG1 kappa (Sigma, Cat No. I5154); Lane 1, Herceptin expressed and secreted using a wild-type signal peptide coding sequence; and Lane 2, Herceptin expressed and secreted using an signal peptide coding sequence according to an embodiment of the present invention.

Results are shown in Table 1 and FIG. 4. More than 10 fold recombinant protein was expressed and secreted using the improved signal peptide coding sequence.

TABLE 1

Level of secreted proteins as measured by ELISA

| Exp. ID | Host cell line | Signal Peptide Coding Sequence | Expression level (mg/L) |
|---|---|---|---|
| 1 | HEK 293 | wild-type (SEQ ID No: 3) | 9.30 |
| 2 | HEK 293 | improved (SEQ ID No: 1) | 103.54 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated nucleic acid molecule for enhanced recombinant expression and secretion of a polypeptide from a cell, the nucleic acid molecule comprising a first polynucleotide sequence encoding a signal peptide operably linked to a second polynucleotide sequence encoding the polypeptide, wherein
   the first polynucleotide sequence and the second polynucleotide sequence are not endogenously operably linked in the cell,
   the first polynucleotide encodes a messenger RNA (mRNA) that comprises at least one hairpin structure immediately downstream of the initiation codon, and
   when expressed in the cell, the signal peptide directs the secretion of the polypeptide from the cell, resulting in enhanced recombinant expression and secretion of the polypeptide from the cell.

2. The isolated nucleic acid molecule of claim 1, wherein the first polynucleotide sequence encodes a signal peptide having an amino acid sequence identical to that of the native signal peptide for the polypeptide in the cell.

3. The isolated nucleic acid molecule of claim 1, wherein the first polynucleotide sequence encodes a signal peptide having an amino acid sequence different from that of the native signal peptide for the polypeptide in the cell.

4. The isolated nucleic acid molecule of claim 1, wherein the at least one hairpin structure has a free energy (ΔG) of about −30 Kcal/mol to about −6.8 Kcal/mol.

5. The isolated nucleic acid molecule of claim 1, wherein the at least one hairpin structure has a stem of about 6 to 25 base pairs.

6. The isolated nucleic acid molecule of claim 1, wherein the mRNA comprises two hairpin structures immediately downstream of the initiation codon.

7. The isolated nucleic acid molecule of claim 6, wherein the mRNA comprises about 1 to 10 nucleotides that participate in the formation of either of the two hairpin structures.

8. The isolated nucleic acid molecule of claim 6, wherein the distance between the two hairpin structures is about 1 to 10 nucleotides.

9. The isolated nucleic acid molecule of claim 1, wherein the first polynucleotide sequence has at least about 55%, 60%, 65%, 70%, 75%, 80%, 85%, 90%, 95% or 100% sequence identity to SEQ ID NO: 1.

10. A vector comprising the nucleic acid molecule of claim 1.

11. A recombinant cell comprising the nucleic acid molecule of claim 1.

12. A method for obtaining enhanced recombinant expression and secretion of a polypeptide from the cell, the method comprising:
    obtaining a nucleic acid molecule according to claim 1;
    introducing the nucleic acid molecule into the cell to obtain a recombinant cell; and
    growing the recombinant cell under conditions to allow enhanced recombinant expression and secretion of the polypeptide from the cell.

13. The method of claim 12, further comprising isolating the polypeptide from the extracellular environment of the cell.

14. The method of claim 12, wherein the polypeptide is selected from the group consisting of Herceptin (trastuzumab), Erbitux, Avastin (bevacizumab), Humira (adalimumab), Rituxan (rituximab), Lantus (insulin glargine), Factor IX, Factor VIII, γ-Interferon, Interleukin 2, Human growth hormone (HGH), Tissue plasminogen activator (TPA), Epo (Erythropoietin), Aranesp, Orencia, Stelare, and Vectibix.

15. An isolated nucleic acid molecule comprising a polynucleotide sequence encoding a signal peptide, the polynucleotide sequence having at least about 55%, 60%, 65%, 70%, 75%, 80%, 85%, 90%, 95% or 100% sequence identity to SEQ ID NO: 1.

16. The isolated nucleic acid molecule of claim 15 comprising SEQ ID NO: 1.

17. The isolated nucleic acid molecule of claim 16 further comprising a second polynucleotide sequence encoding a polypeptide operably linked to SEQ ID NO:1.

18. A method of obtaining an optimized polynucleotide that encodes an optimized signal peptide for enhanced recombinant expression and secretion of a polypeptide, the method comprising:
    obtaining a polynucleotide encoding a signal peptide; and
    substituting one or more nucleotides in the polynucleotide to obtain the optimized polynucleotide encoding the optimized signal peptide, and the optimized polynucleotide encoding a messenger RNA comprising at least one hairpin structure immediately downstream of the initiation codon.

19. The method of claim 18, wherein the substituting step comprises a synonymous substitution.

20. The method of claim 19, wherein the substituting step comprises a non-synonymous substitution.

* * * * *

SEQUENCE LISTING

```
<160> NUMBER OF SEQ ID NOS: 3

<210> SEQ ID NO 1
<211> LENGTH: 57
<212> TYPE: DNA
<213> ORGANISM: Artificial Sequence
<220> FEATURE:
<223> OTHER INFORMATION: Improved Ig H-chain V-region 3 signal peptide
      coding sequence

<400> SEQUENCE: 1
atgggatgga gctgtattat tctgttcctg gtggctaccg ctactggagt gcattct        57

<210> SEQ ID NO 2
```

```
<211> LENGTH: 19
<212> TYPE: PRT
<213> ORGANISM: Mus musculus

<400> SEQUENCE: 2

Met Gly Trp Ser Cys Ile Ile Leu Phe Leu Val Ala Thr Ala Thr Gly
1               5                   10                  15

Val His Ser

<210> SEQ ID NO 3
<211> LENGTH: 57
<212> TYPE: DNA
<213> ORGANISM: Mus musculus

<400> SEQUENCE: 3
atgggatgga gctgtatcat cctcttttg gtagcaacag ctacaggtgt ccactcc         57
```